United States Patent
Barthes

(10) Patent No.: US 6,845,775 B1
(45) Date of Patent: Jan. 25, 2005

(54) SURGICAL VIEWING DEVICE WITH DISPLAY SCREEN CAPABLE OF BEING STERILIZED

(76) Inventor: Michel Barthes, 9, rue Ernest André, 78110 Le Vésinet (FR)

( * ) Notice: Subject to any disclaimer, the term of this patent is extended or adjusted under 35 U.S.C. 154(b) by 387 days.

(21) Appl. No.: 10/088,928

(22) PCT Filed: Sep. 19, 2000

(86) PCT No.: PCT/FR00/02591

§ 371 (c)(1),
(2), (4) Date: Mar. 20, 2002

(87) PCT Pub. No.: WO01/21086

PCT Pub. Date: Mar. 29, 2001

(30) Foreign Application Priority Data

Sep. 20, 1999 (FR) .............................. 99 11734

(51) Int. Cl.[7] .............................................. A61B 19/00
(52) U.S. Cl. ........................ 128/849; 600/101; 600/133; 348/77
(58) Field of Search ................................ 128/856, 849, 128/851, 852, 853; 600/101, 102, 133, 121, 122; 348/77; 206/438, 466, 305, 829; 174/17.05; 200/302.2; 150/165

(56) References Cited

U.S. PATENT DOCUMENTS

| | | | |
|---|---|---|---|
| 4,894,748 A | | 1/1990 | Shefet |
| 4,963,693 A | | 10/1990 | Kodl |
| 5,111,222 A | | 5/1992 | Hayakawa et al. |
| 5,433,221 A | * | 7/1995 | Adair .......................... 128/849 |
| 5,732,712 A | * | 3/1998 | Adair .......................... 128/849 |
| 5,765,565 A | * | 6/1998 | Adair .......................... 128/849 |
| 5,812,188 A | * | 9/1998 | Adair .......................... 348/77 |
| 5,957,831 A | * | 9/1999 | Adair .......................... 600/101 |
| 5,970,980 A | * | 10/1999 | Adair .......................... 128/849 |

FOREIGN PATENT DOCUMENTS

| | | |
|---|---|---|
| DE | 19907642 A | 8/1999 |
| GB | 2064879 A | 6/1981 |
| JP | 02136123 | 5/1990 |
| JP | 08150114 | 6/1996 |
| JP | 08280610 | 10/1996 |
| WO | WO98/02107 | 1/1998 |
| WO | WO98/03013 | 1/1998 |
| WO | WO98/27561 | 6/1998 |

* cited by examiner

*Primary Examiner*—Fadi H. Dahbour
(74) *Attorney, Agent, or Firm*—Blakely Sokoloff Taylor & Zafman

(57) ABSTRACT

The invention concerns a device for observing a surgical field, comprising a flat monitor video (15, 40) and a chamber (20, 30) capable of being sterilized and forming a sealingly closed sterility barrier around the monitor video (15, 40), wherein the chamber (20, 30) is sufficiently sealed to maintain internal excess pressure or negative pressure applied on the closure of the chamber (20, 30), and the chamber (20, 30) is with an internal pressure sensor (160) for actuating alarm means when the excess pressure or negative pressure is no longer present, the assembled device being capable of being sterilized to infinity and of being used in all types of sterilized rooms, for example in a surgery or in a laboratory.

11 Claims, 2 Drawing Sheets

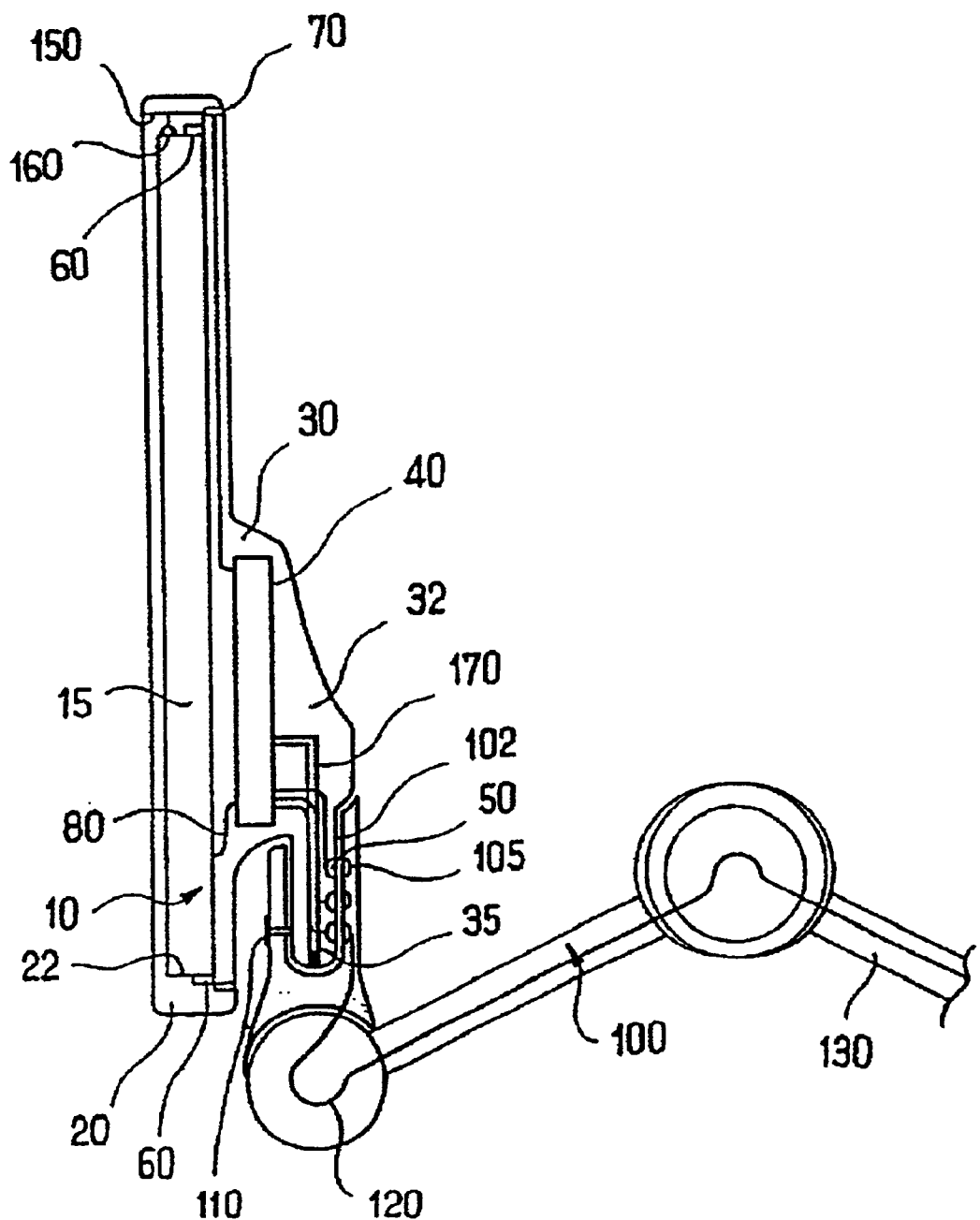
FIG_1

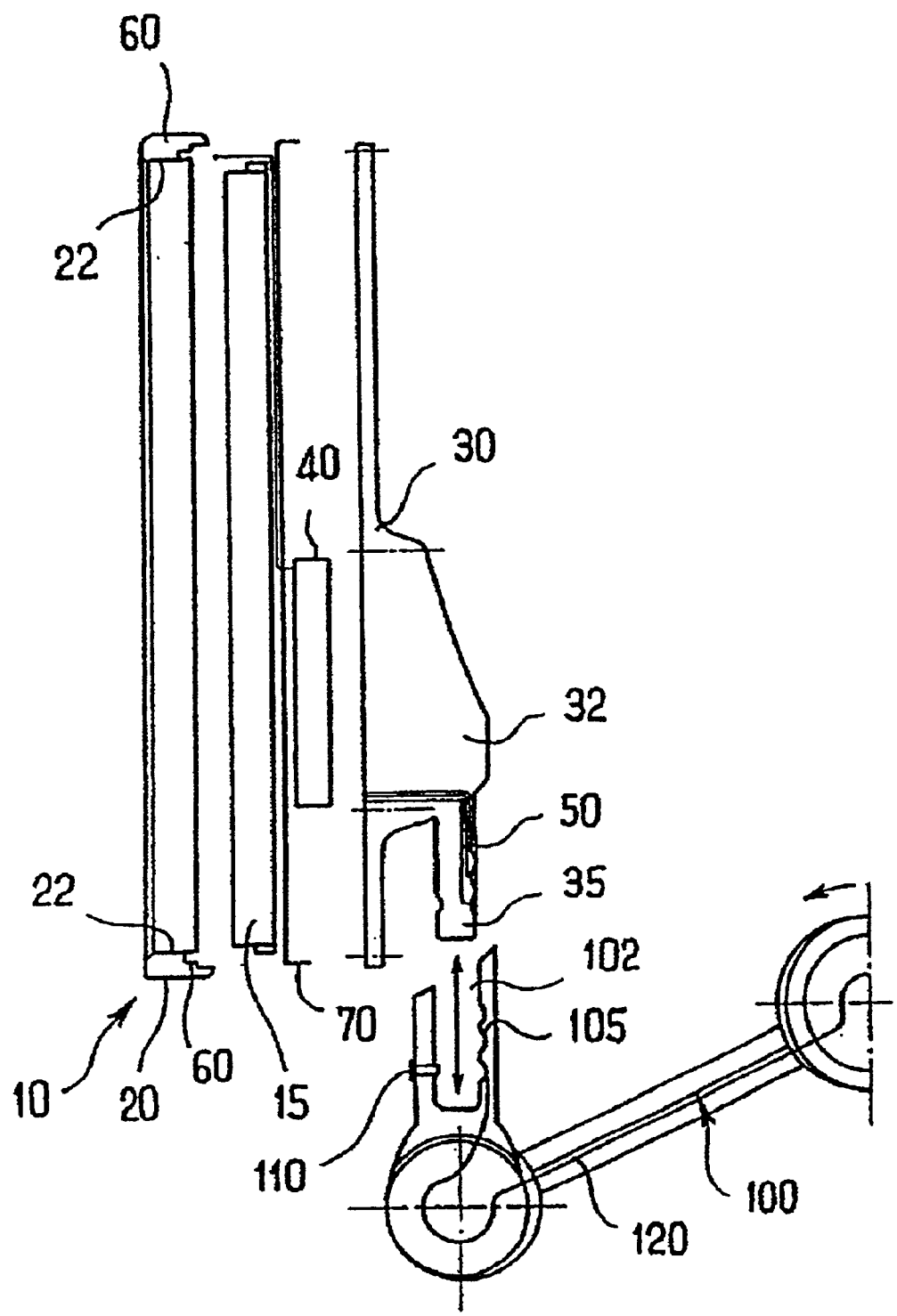
FIG_2

SURGICAL VIEWING DEVICE WITH DISPLAY SCREEN CAPABLE OF BEING STERILIZED

BACKGROUND OF THE INVENTION

1. Field of the Invention

The invention relates to devices for observing a surgical field, and in particular to such devices which are coupled to an endoscope.

Such devices are traditionally made up of an endoscopic camera which the surgeon guides manually in the patient's body, and of a video monitor which is placed a few meters away and on which the image recorded by the camera is displayed.

The surgeon uses a surgical instrument, guiding its leading end which appears on the screen.

Ordinary television screens of this kind are difficult to sterilize, so that surgeons have for many years contented themselves with keeping these screens away from the patient.

2. Description of Related Art

In the document WO 98/02107, a sterile enclosure for a flat screen has been proposed, consisting simply of a flexible envelope having substantially the shape of the screen and continuing via a sleeve around a part of a cord for powering the screen and for exchange of signals.

This document proposes closing this envelope around the cord and permanently drawing air inside this envelope in order to press it flat against the screen.

According to one variant, this document proposes placing a rigid enclosure around the screen, this enclosure having connection orifices intended to be hermetically closed when connected.

In this variant, after connection, a totally sealed envelope is obtained which permits sterilizing of the assembly by immersion without having to remove the screen from the enclosure.

However, such a device has an important disadvantage in that it is difficult to guarantee its sterility.

The sealing of the assembly rests entirely on the sealing between the enclosure and the cable connectors. This sealing is difficult to guarantee, especially as the cables are often moved or pulled and the connection is subjected to high forces. The hermetic closure between the sterile outside and the nonsterile inside of the chamber thus depends on particularly fragile means.

In addition, the rigid enclosure must be able to be opened and comprises for this purpose at least two parts which can be detached from one another. Complete sealing at the junction between these two components cannot be guaranteed for an indefinite number of sterilizations of the chamber, and air communication between the inside and the outside of the enclosure takes place at the level of this junction.

Such a device therefore cannot be considered as reliable.

The main object of the invention is to remedy this disadvantage.

BRIEF SUMMARY OF THE INVENTION

To do so, the invention makes available a device for observing a surgical field, said device comprising a flat video monitor and a chamber which is sterilizable and which forms a sterility barrier closed in a sealed manner around the monitor, characterized in that the chamber is sufficiently sealed to maintain an internal overpressure or underpressure applied upon closure of the chamber, and in that the chamber is provided with an internal pressure sensor which can activate alarm means in the event of the internal overpressure or underpressure disappearing, the assembled device being sterilizable to infinity and being able to be used in sterile areas of all types, for example in medical areas or in a laboratory.

DESCRIPTION OF THE DRAWINGS

Other characteristics, aims and advantages of the invention will become apparent from the detailed description which follows and in which reference is made to the attached figures, in which:

FIG. 1 shows a surgical viewing device according to the invention, in cross section;

FIG. 2 shows the same device in the same cross section, in an exploded view.

DETAILED DESCRIPTION OF THE INVENTION

The present viewing device is made up of a video display assembly 10 and of an articulated arm 100 forming a support for the display assembly 10.

The display assembly 10 is made up of two main assemblies, namely a video monitor enclosed in a sealed chamber.

The video monitor is in the form of a liquid crystal screen 15 and an electronic module 40 connected to this screen by a wire connection 80.

The screen 15 is here an active-matrix liquid crystal screen (LCD), of the type with microtips, from plasma technology, or from transistorless technology of the DEL type (Digital Electronic Luminescence).

In this embodiment, these two elements 15 and 40 are maintained in position relative to one another by the sealed chamber.

For this purpose, the latter is formed by two components 20 and 30, each having a plane and rectangular general shape and with dimensions slightly greater than those of the screen 15.

The element 30 will cover the whole rear face of the screen 15. For this purpose, it has a part of overall rectangular shape and four rectilinear edges along the four edges of the screen 15.

In its central part, this rear panel 30 extends away from the screen 15 in the form of a hump-shaped undulation whose concave part directed towards the screen 15 forms, at the rear of the latter, a cavity for receiving the electronic module 40, and whose rear convex part continues as a sleeve 35 intended to be engaged in the support 100.

More precisely, the internal cavity formed by this hump 30 has a parallelepipedal shape complementing that of the module 40. Once the module 40 is in place in the internal cavity of this hump 30, and the screen 15 is connected to the module 40, the screen 15 receives via its front face the component 20 in the general form of a parallelepipedal receptacle whose bottom forms the front panel of the screen 15 and whose four raised edges cover the four edges of the screen 15.

These four edges are high enough also to cover the four free edges of the rear panel 30 extending beyond the edges of the screen 15 and to cooperate with these, so that the two elements 20 and 30 form a closed chamber around the screen 15 and the module 40.

To afford particularly reliable sealing of the assembly, a Teflon seal labelled 70 is arranged between these two elements 20 and 30, in particular at their edge junction.

As can be seen from the exploded view in FIG. 2, this seal 70 is in this case a sheet which covers the whole of the front face of the rear panel 30 and is folded back about the four free edges of the rear panel 30. These folds are sandwiched between the free edges of the panel 30 and the inner faces of the raised edges of the front cover 20.

It will also be noted that the raised edges of the cover 20 form a bulge 22 on their inner face, the rear end of which bulge 22 stops before the end of the raised edge, in the form of a flat shoulder facing the panel 30 and intended to bear against a peripheral portion of the front face of the panel 30.

Distributed about the cover 20, this bulge 22 has threaded seats adapted to receive fixing screws which pass through the rear panel 30. This screwing ensures a particularly strong pressing of the bulge 22 on the panel 30 with the Teflon sheet sandwiched in between.

The sheet 70 is thus sandwiched not only between the lateral ends of the panel 30 and the inner face of the raised edge of the cover 20, but also between the bulge 22 and the front face of the panel 30 in such a way that the sheet 70 is subjected, irrespective of the position of the periphery of the panel 30, to two gripping forces perpendicular to each other.

The sheet 70 here covers the whole of the panel 30 but it can be replaced by an annular element, for example of plane shape and parallel to the panel 30, or of cylindrical shape and covering only the lateral edge of the panel 30, or else of bracket-shaped cross section in order to receive both the lateral end and the peripheral edge of the front face of the panel 30.

It will also be noted that the bulge 22 advantageously forms a groove open to the rear and inside of the cover 20 and receiving a complementary peripheral rib of the screen 15 in order to hold the latter by gripping it between the bulge 22 and the panel 30.

The present components 20 and 30 are made of glass, which gives them a high degree of rigidity and complete transparency. This glass advantageously includes embedded particles able to form a barrier with respect to interferences which could adulterate the images displayed or various control signals described below.

The chamber can be made up of several components, of which only the part covering the front face of the screen 15 is made transparent.

The chamber can also be made of plastic, for example of Makrolon DP1-1262 marketed by Bayer, or of Noryl.

The electronic module 40 is connected to the screen 15 via a connection 80 simply arranged in the cavity of the hump 32.

The module 40 is also continued via a second double connection which runs along the front face of the panel 30 and the raised edge of the cover 20 and opens out in the inner space of the chamber and has a pressure sensor 160 at this end. This double connection forms a second line of transmission which opens out on the front face of the cover 20 and has a voice sensor 150.

The pressure sensor 160 sends a measurement signal to the electronic module 40 which then compares the measured pressure to a threshold value authorized for the internal pressure. This authorized internal pressure is, in the present example, a pressure markedly higher than atmospheric pressure. Indeed, the sealed chamber is set at an overpressure and then closed hermetically in a preliminary step, and the electronic module monitors the value of this overpressure during the course of time.

In the event of escape from the sealed chamber, that is to say in the event of the sealing between the sterile outside atmosphere and the nonsterile internal parts of the chamber being lost, an internal pressure drop detected by the electronic module 40 as falling below the threshold value is translated by the module 40 displaying on the screen 15 a visual warning indicating this loss of pressure.

According to one variant of the invention, the chamber can also be subjected to an initial underpressure, the module 40 alerting the user when this underpressure attenuates in an undesired manner.

The present device is provided with a channel 170 for fluid communication connecting the internal cavity of the hump 32 to the end of the support sleeve 35. This channel 170 is closed at its end by a nonreturn valve.

After the chamber has been assembled, the sleeve 35 is engaged in a device which can inject a gas into the channel 170 until a sufficient pressurization of the chamber is obtained. Once the chamber has been separated from this pressurizing device, it maintains its internal pressure, by virtue of the arrangements which have just been described, with a particularly high degree of reliability.

The present display assembly can be sterilized several times without loss of overpressure, both by immersion and also by a process based on irradiation, such as the known STERRAD procedure.

A material of the Sterrad type permits sterilization at low temperature (about 45°) for a plasma gas of the hydrogen peroxide type and application of a radio frequency or gamma rays. The sterilization can also be carried out, for example, with a standard disinfecting product of the SIDEC type.

The assembly thus closed and sealed can therefore be used several times in an operating theater, with sterilization between each use. At each use, the operating team can check on the screen that the loss of pressure warning is not present and can thereby gain a guarantee of complete sealing of the chamber, and thus of its sterility.

The screen is placed a few centimeters above the patient's body, for example above the surgeon's hands, so that the practitioner only has to accommodate his vision over a short distance, which limits eye fatigue.

The present electronic module 40 additionally analyzes the signals from the sensor 170 in order, on the basis of these signals, to control different functions of the present screen 15 and also to transmit controls to other devices such as an endoscopy instrument (not shown).

To transmit or receive the images to be displayed, the module 40 has wire connections passing through the rear part 32 of the chamber and opening out on the rear outer face of this part. These wire connections have at their end electrical contacts 50 which are hermetically connected to the material constituting the part 32, in order to ensure a high degree of sealing at their level. This sealed connection with contacts is in this case a sealed connection of the type with contact balls.

More precisely, the electrical connections run longitudinally along the sleeve 35 and the metal contacts 50 are distributed along the sleeve 35.

The support 100 is an articulated support, with arms and articulations, the end portion of which forms a cavity 102 complementing the arm 35, in order to receive the arm 35 and thus maintain the display assembly in the desired position. The articulations of the support 100 are preferably intended to be sealed for easy sterilization, in particular by immersion, of this support.

This cavity 102 of the support is also provided on its inner face with metal contacts which bear against the oil contacts of the arm 50. These contacts are continued by electrical connections running through the assembly of arms and articulations of the support 100 and adapted to permit the movements of the articulations.

Thus, the engagement of the arm 35 in the corresponding cavity 102 of the support produces a mechanical support of the display assembly 10 and a signal exchange connection between the electronic module 40 and external electronic arrangements such as the endoscopy instruments and cameras (not shown).

A pin 110 is provided which passes through a lateral wall of the cavity 102 and lodges in a corresponding bore in the arm 35. This pin 110 thus secures the arm 35 against accidental release from the cavity 102 and against rotation of the arm 35 in the cavity 102.

In the present example, the contacts and connections of the support with the display assembly also convey electrical energy for powering the module 40 and the screen 15.

According to one variant, the module 40 can also include a battery which is charged before joining-together and pressurization of the display assembly 10.

According to another variant, the module 40 is continued via at least one electrical connection whose end carries an antenna for emission, reception, or both, of electromagnetic waves. The connections can also carry a light emitter, a light sensor or both. The sensors and emitters of the display assembly are, for example, infrared sensors and/or emitters. These elements for emission or reception of electromagnetic waves or light are preferably embedded in the material constituting the component 30, at a location close to the outer surface of the component 30. Thus, means for electromagnetic reception comprising a reception antenna are preferably placed at a location where the chamber has, between this antenna and the outside, a thickness which is less than the average thickness of the chamber.

The energy for powering the screen 15 and the module 40 is thus preferably transmitted in the form of such electromagnetic or light waves.

In these variants, the internal walls of the cavity 102 advantageously have electromagnetic or light receivers/emitters, each corresponding to the emitters/receivers of the display assembly.

Such contactless connection elements can also be elements of the induction type for transmitting signals or for transmitting the power.

In view of the features described above, the chamber and the elements which it surrounds form an assembly which is sterilizable to infinity, that is to say without consideration of a limited number of sterilizations fixed in advance. This is because the possible discontinuation of the sterilizations is indicated by the warning given by virtue of the pressure sensor. The internal pressure sensor or sensors guarantee effective and repeated sterilization and, in the absence of a warning, guarantee the perfect state of functioning and sealing of the device, in particular before and after sterilization. The assembly described can be used in sterile areas of any type, whether medical or not, such as an operating theater, laboratory, or areas where work is being carried out on bacteria whose development may be modified by the presence of nonsterile objects.

What is claimed is:

1. A device for observing a surgical field, comprising a flat video monitor (15, 40) and a chamber (20, 30) which is sterilizable and which forms a sterility barrier closed in a sealed manner around the monitor (15, 40), characterized in that the chamber (20, 30) is sufficiently sealed to maintain an internal overpressure or underpressure applied upon closure of the chamber (20, 30), and in that the chamber (20, 30) is provided with an internal pressure sensor (160) which can activate alarm means in the event of the internal overpressure or underpressure disappearing, the assembled device being sterilizable to infinity and being able to be used in sterile areas of all types, for example in medical areas or in a laboratory.

2. The device as claimed in claim 1, characterized in that the chamber (20, 30) is provided with an electrical connection passing through it from the inside to the outside and forming at its outer end an electrical contact (50) connected to the chamber (20, 30) in a sealed manner.

3. The device as claimed in one of the preceding claims, characterized in that it comprises means for electromagnetic reception which are connected electrically to the monitor (15, 40) and are intended to receive electromagnetic energy for powering the monitor (15, 40).

4. The device as claimed in claim 1, characterized in that it comprises means for electromagnetic reception comprising a reception antenna arranged at a location where the chamber (20, 30) has, between this antenna and the outside, a thickness which is less than the average thickness of the chamber (20, 30).

5. The device as claimed in claim 4, characterized in that the means for electromagnetic reception are also intended to send electromagnetic signals to a reception device outside the chamber.

6. The device as claimed in claim 1, characterized in that it comprises means for emitting or receiving infrared waves.

7. The device as claimed in claim 6, characterized in that the means for emitting or receiving infrared waves are intended to collect light energy for powering the monitor (15, 40).

8. The device as claimed in claim 1, characterized in that it comprises a support (100) for the chamber, said chamber (20, 30) and said support (100) forming complementary engagement means (35, 102) for maintaining the chamber (20, 30) on the support (100), these engagement means (35, 102) having complementary connection means so that the engagement also effects an exchange connection between the chamber (20, 30) and the support (100).

9. The device as claimed in claim 8, characterized in that the chamber (20, 30) forms an arm (35) intended to be inserted in a complementary cavity (102) of the support (100), and in that the arm (35) and the cavity (102) comprise arrangements for locking (100) the arm (35) in the cavity (102) and opposing a rotation of the arm (35) in the cavity (102).

10. The device as claimed in claim 1, characterized in that the chamber (20, 30) is made of glass.

11. The device as claimed in claim 1, characterized in that the chamber comprises at least two elements (20, 30) and a Teflon seal (70) arranged between at least two respective parts of these two elements (20,30).

* * * * *